(12) United States Patent
Lorenz

(10) Patent No.: US 6,433,025 B1
(45) Date of Patent: Aug. 13, 2002

(54) METHOD FOR RETARDING AND PREVENTING SUNBURN BY UV LIGHT

(75) Inventor: R. Todd Lorenz, Kailua-Kona, HI (US)

(73) Assignee: Cyanotech Corporation, Kailu-Kona, HI (US)

( * ) Notice: Subject to any disclaimer, the term of this patent is extended or adjusted under 35 U.S.C. 154(b) by 0 days.

(21) Appl. No.: 09/549,317

(22) Filed: Apr. 13, 2000

(51) Int. Cl.$^7$ .................... A61K 31/07; A61K 31/045; A61K 31/12; A61K 9/00; A61K 7/00; A61K 7/42
(52) U.S. Cl. .................... 514/725; 514/724; 514/691; 424/400; 424/401; 424/59
(58) Field of Search .............................. 424/400, 401, 424/59; 514/691, 724, 725

(56) References Cited

U.S. PATENT DOCUMENTS

| | | | | |
|---|---|---|---|---|
| 3,920,834 A | * | 11/1975 | Klaui et al. | ................. 424/305 |
| 5,527,533 A | * | 6/1996 | Tso et al. | ................... 424/422 |

FOREIGN PATENT DOCUMENTS

| | | | |
|---|---|---|---|
| JP | 63083017 A | * | 4/1988 |
| JP | 09143063-a | * | 6/1997 |

OTHER PUBLICATIONS

McCarthy et al. "Beach Holiday Sunburn: The Sunscreen Paradox and Gender Differences" Jul. 1997.
Cavallo et al. "SunBurn" 1986.
Bangha et al. "Suppression of UV–Induced Erythema by Tropical Treatment With Melatonin" 1997.
Potts, Jerome, F. "Sunlight, sunburn and sunscreens" 1990.
Ritter et al. "Modulation of Ultraviolet Light–Induced Epidermal Damage: Beneficial Effect of Tocopherol" 1997.
Matthews–Roth et al. "Carotenoid Dose Level and Protection Against UV–B Induced Skin Tumors" 1985.
Ribaya–Mercado, et al. "Effect of Beta–Carotene Supplementation on the Human Sunburn Reaction" 1995.
Eberlein–Konig et al. "Protective Effect Agaisnt Sunburn of Combined Systemic Ascorbic Acid (vitamin c) and d–a–tocopherol (vitamin e)" 1998.
Green et al. "Daily Sunscreen Application and Betacarotene Supplementation in Prevention of Basal–Cell and Sqaumous–Cell Carcinomas of the skin: A Randomized Controlled Trial" 1999.
Franklin et al. "The Role of the (6–4) Photoproduct in Ultraviolet Light–Induced Transition Mutations in Ecoli" 1986.
Park et al. "Signaling Pathways Mediating Melanogenesis" 1999.
Bickers "Sun–Induced Disorders", 1985.
Marks, "Photoprotection and prevention of melanoma" 1999.
Ibbotson et al "The Effects of Radicals Compared with UVB as Initiating Species of the Induction of Chronic Cutaneous Photodamage" 1999.

* cited by examiner

*Primary Examiner*—Raymond Henley, III
*Assistant Examiner*—Donna Jagoe
(74) *Attorney, Agent, or Firm*—Devine, Millimet & Branch, P.A.

(57) ABSTRACT

Astaxanthin is a potent antioxidant, over 500 times more powerful than Vitamin E and 10 times stronger than other carotenoids such as zeaxanthin, lutein, canthaxanthin and beta-carotene. Astaxanthin has also been shown to enhance and modulate the immune system. Disclosed is a method and treatment for retarding and preventing sunburns. The method comprises administering a source of astaxanthin in a therapeutically effective amount to prevent and retard sunburns.

20 Claims, No Drawings

METHOD FOR RETARDING AND PREVENTING SUNBURN BY UV LIGHT

FIELD OF THE INVENTION

This invention relates to the treatment and prevention of sunburns by UV light exposure. More particularly the invention relates to a method for prevention of sunburns using, as a basis, the protective properties of astaxanthin. Most particularly, the invention relates to prevention of sunburns using orally administered astaxanthin.

BACKGROUND OF THE INVENTION

Tanning is pigmentation of the skin due to the synthesis and dispersion of melanin in the epidermis. It is of great cosmetic and societal significance and a key physiological defense against sun-induced injuries such as sunburn, photocarcinogenesis and photoaging. However, during recent decades, there has been a dramatic increase in skin cancers, including melanoma, due to habitual sun exposure. At present, in the United States, about one in 75 individuals are projected to develop malignant melanoma during their lifetime. Unfortunately, progress in preventing sun-related injuries has been slow, in part due to lack of understanding of the molecular mechanisms involved in pigmentation.

There have been increasing incidence and mortality rates due to melanoma in most countries where they are being recorded. The highest incidences occur in areas with the highest flux of solar radiation such as the southern US, regions near the equator or at higher elevations. Ultraviolet radiation (UVR) increases about 4% for every 1000 feet in elevation. Lighter-skinned individuals are affected more frequently and severely. Significant transmission of UVR may occur through some types of clothing resulting in sunburned skin. The initial approach in many countries has been to develop some form of early detection program in an attempt to diagnose and treat at a curable stage the melanomas that are occurring now. The long-term morbidity and mortality associated with chronic sun exposure is related primarily to the development of cutaneous neoplasms, including basal cell carcinoma and malignant carcinoma.

Primary prevention of melanoma is a more long-term approach to the problem which many countries are now considering and a number are actively pursuing. A survey conducted at Galveston beach showed that the likelihood of sunburn increased with increasing duration of sun exposure, with 100% of subjects experiencing sunburn after 4.5 hours of exposure. Men exhibited a significantly higher frequency of sunburn, employed fewer sun-protective measures, and demonstrated less knowledge concerning sun safety information and skin cancer than women. The information suggests a need for greater educational efforts directed toward changing public attitudes about preventing sunburn, especially those of men, that currently lead to high-risk sunbathing behavior (McCarthy et al. 1999).

Sunburns are an acute inflammation reaction of the skin and tissue just beneath it that follows excessive exposure of the skin to UVR. The affected area becomes red, hot, tender, and swollen and in severe cases blisters may form. The ultraviolet spectrum can be divided in UVA (320–400 nm), UVB (290–320 nm) and UVC (200–290 nm), wavelengths less than 290 nm are filtered out in the outer atmosphere and are not encountered at sea level. About 65% of the total UVR reaches the earth between 10 AM and 2 PM. UVB radiation are high intensity rays absorbed by the surface of the skin and the primary cause of sunburns, erythema and intermediate skin damage. UVA rays are lower intensity but penetrate below the skin surface causing long-term damage such as premature wrinkling. UVA comprises the majority of the total UVR reaching the surface of the earth (about 90% at midday) and accounts for a significant percentage of the acute and chronic cutaneous effects. UVC and UVB produce damage primarily by the formation of cyclobutane pyrimidine dimers of DNA. Pyrimidine dimers are 80–90% of the UV-light induced DNA photoproducts, with the remainder being pyrimidine (6,4) pyrimidone (Franklin and Haseltine, 1986).

Recent concern about stratospheric ozone depletion has contributed to the desire for the primary prevention approach. There are epidemiological data associating the risk of melanoma with increased exposure to sunlight in people with fair skin. The exact spectrum of radiation in sunlight which is responsible for these tumors is not known, although the ultraviolet range is believed to be most important, particularly UVB but probably also UVA. Studies show that sunburns in childhood result in increased risk of melanoma later in life. Protecting children is especially important since more than half of a person exposure occurs before the age of 20. It is estimated that approximately 80% of the skin changes commonly thought of as skin aging (premature wrinkles, leathery skin, freckles, dark spots) are actually due to sun exposure and not to the actual age of the skin. The aging process affects the skin's ability to protect itself. The rate of cell protection and turnover slows down with age, making cell repair less effective. The outer layer epidermis of the skin becomes thinner and melanocytes gradually lose their pigment producing ability, thereby reducing protection for the skin.

Skin cancer is the most common type of cancer, about 800,000 cases occur in the US each year. Most skin cancers are either basal cell or squamous type and tend to grow and spread slowly. Nearly 95% can be cured. Malignant melanoma is a much more serious form of skin cancer and is now increasing by about 4% per year. Melanoma was diagnosed in approximately 38,300 Americans in 1996. The overall five-year survival rate for melanoma is 85%. The five-year survival rate for localized disease is 93% and about 82% of melanomas are diagnosed in this earlier stage. The second-most common form of skin cancer, squamous cell carcinoma, appears as nodules or red scaly patches, and can spread if untreated. While the cure rate is relatively high, squamous cell carcinoma results in at least 1,200 deaths per year (Park and Gilchrest. 1999).

Less intense or shorter-duration exposure to UVR results in an increase in skin pigmentation that provides some protection against further UVR-induced damage. The increased skin pigmentation occurs in two phases, immediate pigment darkening and delayed tanning. Intermediate pigment darkening occurs during exposure to UVR and results from oxidation and redistribution of existing melanin. This reaction may fade rapidly or persist for several days. Delayed tanning results from increased synthesis of epidermal melanin and requires 24–72 hours to become visible. With repeated exposure to UVR, the skin thickens due to epidermal hyperplasia and thickening of the stratum corneum.

The minimal single dose of UVR (energy per unit area) required to produce erythema on exposed skin is known as minimal erythema dose (MED). Moderate to severe sunburn occurs at 3–8 MED's. UVR penetrates moist skin more effectively than dry skin. MED's are greater on the limbs than on the face, neck and trunk. Exposure to solar radiation has beneficial benefits of stimulating cutaneous synthesis of vitamin D. However, when skin is subjected to excessive radiation in the ultraviolet range (less than 400 nm), deleterious effects such as sunburn or 'solar erythema' can occur. Solar erythema is associated with microscopic changes in the skin that are detectable within 30 minutes of UVR exposure. The most characteristic changes include formation of epidermal sunburn cells, damaged keratinocytes with hyaline cytoplasm and pyknotic nuclei. Epidermal Langerhans cells and mast cells may decrease while the relative percentage of hypogranulated or degranulated cells may increase. Superficial blood vessels show endothelial swelling, perivenular edema and a mixed perivascular infiltrate. The precise biochemical pathways that lead to the sunburn reaction are not fully understood, but appear to involve multiple mediators including histamine, prostaglandins and cytokines. Sunburns may cause exacerbation of other skin diseases, and trigger recurrence of herpes simplex, lupus, porphyria or other cutaneous disorders. Chronic sunburns and exposure to the sun can lead to multiple deleterious effects including premature aging and wrinkling of the skin (dermatoheliosis), development of pre-malignant lesions (solar keratoses) and various malignant tumors (e.g. basal cell, squamous cell and melanoma). Large freckles known as 'age spots' and scaly growths (actinic keratoses) may develop into skin cancer.

Free radicals of oxygen have been shown to result from and mediate deleterious effects of ultraviolet radiation on the skin. One study showed that the number of sunburn to cells was decreased by treatment with the antioxidant tocopherol, and may result from both direct protection from free radicals and indirect protection by means of increased epidermal thickness. (Ritter E.F. et al, 1997). There is additional evidence that ultraviolet radiation induces the formation of reactive oxygen species and these are implicated as toxic intermediates in the pathogenesis of photoaging. One study examined whether repeated topical treatment with benzoyl peroxide, a source of free radicals, produced the same cutaneous effects as chronic ultraviolet B radiation. These results indicate that repeated administration of benzoyl peroxide produces skin changes in the hairless mouse that qualitatively resemble those produced by ultraviolet B and suggest that common mechanisms may be involved (Ibbotson S.H. et al., 1999).

Exposure of the skin to UVR triggers a chain reaction within skin cells that generates lipid peroxides and other high-energy free radicals. These molecules damage cellular components such as DNA, thereby increasing the risk of skin cancer development. Although the body utilizes an array of antioxidants such as vitamin E, vitamin C, selenium and superoxide dismutase to scavenge these free radicals, they can become quickly depleted under the severe stress of UVR exposure. One study showed that when a 10% solution of vitamin C was applied to the skin of volunteers, the amount of ultraviolet light needed for them to burn increased by an average of 22%. Once they did burn, half of the volunteers experienced much less severe burns than those without the vitamin C solution. In studies with laboratory animals, researchers found that vitamin E acetate, which converts to vitamin E in the body, prevented inflammation, skin sensitivity and skin damage when applied up to 8 hours following UVB exposure. In one human study, supplementation of dietary vitamin E and vitamin C elicited a 21% higher tolerance of MED than the control group (Eberlein-Konig B. et al. 1998).

A double-blind randomized study was designed to examine the influence of the antioxidant, melatonin, on the anti-erythema effect. Topical treatment of the skin with melatonin 15 min before UV irradiation proved to almost completely suppress the development of an UV-induced erythema. In contrast, no significant protective effects of melatonin were observed when it was applied after UV irradiation. The researchers concluded that topically applied melatonin has a clear-cut protective effect against UV-induced erythema. Free radical scavenging of UV-generated hydroxyl radicals and interference with the arachidonic acid metabolism are possible mechanisms of the melatonin action (Bangha E. et al, 1997).

There is some evidence that oral beta-carotene supplementation may lower skin-cancer rates in animals, but there is limited evidence of its effect in human beings (Roth and Krinski, 1985.). One double blind placebo-controlled study examined the effect of beta-carotene supplementation on the human sunburn response. However, the data suggested that oral beta-carotene supplementation is unlikely to modify the severity of cutaneous photodamage in normal individuals to a clinically meaningful degree (Garmyn M. et al. 1995). In a community-based randomized trial, individuals were assigned to four treatment groups: daily application of a sun protection factor 15-plus sunscreen to the head, neck, arms, and hands, and beta-carotene supplementation (30 mg per day); sunscreen plus placebo tablets; beta-carotene only; or placebo only. The endpoints after 4.5 years of follow-up were the incidence of basal-cell and squamous-cell carcinomas both in terms of people treated for newly diagnosed disease and in terms of the numbers of tumors that occurred. The 1383 participants underwent full skin examination and 250 of them developed 758 new skin cancers during the follow-up period. There were no significant differences in the incidence of first new skin cancers between groups randomly assigned daily sunscreen and no daily sunscreen. Similarly, there was no significant difference between the beta-carotene and placebo groups in incidence of either cancer. In terms of the number of tumors, there was no effect on incidence of basal-cell carcinoma by sunscreen use or by beta-carotene but the incidence of squamous-cell carcinoma was significantly lower in the sunscreen group than in the no daily sunscreen group (1115 vs 1832 per 100,000). The authors concluded that there was no harmful effect of daily use of sunscreen in this medium-term study. Cutaneous squamous-cell carcinoma, but not basal-cell carcinoma seems to be amenable to prevention through the routine use of sunscreen by adults for 4.5 years. There was no beneficial or harmful effect on the rates of either type of skin cancer, as a result of beta-carotene supplementation (Green et al. 1999).

There are numerous risk factors for the development of malignant melanomas including genetic and environmental aspects. The most important genetic risk factor is a mutation in the CDKN2A gene, which is a tumor suppressor-gene that regulates the cell cycle. In addition, the familial dysplastic nevus syndrome shows a marked risk for the development of malignant melanoma. Patients with xeroderma pigmentosum have an inability to repair UV-induced DNA defects. This constellation leads to early development of epitheliomas and malignant melanomas. Constitutional risk factors are fair-red hair and blue eyes with a high tendency for sunburns. The most important environmental factor is UV-exposition. Sunburns before the age of 15 and the total 10 cumulative UV-dosage are high impact risk factors. The most important preventive measures are to check the whole skin at a regular base in a patient with the familal dysplastic nevus syndrome, and in addition all such persons should wear a hat, trousers, shirt and glasses. Furthermore direct sun exposure should be avoided during noon time. (Itin P.H., 1999).

In general, prevention of sunburn should be the most important goal, but sunburn often cannot be avoided. Avoiding sun between the period of peak solar radiation from 10 AM to 3 PM and wearing protective clothing including hats is a major preventive method. Sunscreens have assumed a major component of primary prevention programs based on their convenience of use. Sunscreens work by absorbing, reflecting or scattering the sun's rays on the skin and are labeled with sun protection factor (SPF) numbers. If one sunburns in 10 minutes, a SPF 15 formula will protect the skin for 15 times longer, or 150 minutes. These products protect predominantly in the UVB range for which there is a SPF grading, as well as having some activity in the UVA range. Regular use of sunscreens with an adequate sun protection factor (SPF) applied 30 minutes before exposure to sun can help protect skin. Chemical barriers are used in most sunscreens. PABA (para-amino benzoic acid) PABA esters and their derivatives such as octyl dimethyl PABA diffuse into the stratum corneum and bind to protect skin from UVR. However, PABA agents may stain clothing or cause contact dermatitis, and are not recommended for use on children less than 6 months of age. Other chemical blocking agents include cinnamates, salicylates, anthranilates and benzophenones or various combinations. However, all of these chemicals photodecompose into unknown compounds and the long-range safety effects have not been studied. Physical barriers such as zinc oxide, talc, and titanium dioxide provide excellent protection but are often not used because they are less appealing cosmetically. Oral canthaxanthin tablets have also been marketed as a form of 'sunless tanning' and protection against UVR (Marks R. 1999). Aspirin, ibuprofen, acetaminophen and other non-steroidal anti-inflammatory drugs (NSAID's) have anti-prostaglandin effects and are useful to relieve pain and inflammation when given early. Systemic steroids may shorten the course and reduce pain of sunburn when given early and in relatively high doses. Topical steroids show minimal, if any benefit.

Algae and Astaxanthin:

Although natural sources of astaxanthin are numerous, nearly all are found in very low concentrations. Astaxanthin is quite common in nature, especially in the marine environment and is probably best known for providing the pinkish-red hue to the flesh of salmon and trout, as well as shrimp, lobsters and crayfish. These animals obtain astaxanthin in their diet from zooplankton, insects or crustaceans that have accumulated astaxanthin from phytoplankton.

The green algae *Haematococcuspluvialis* provides the most concentrated natural source of astaxanthin known, from 10,000–40,000 ppm (mg/kg) astaxanthin in addition to other important carotenoids such as beta-carotene, lutein and canthaxanthin. Whereas, the flesh of wild Atlantic salmon contain approximately 5 ppm of astaxanthin, Coho salmon about 14 ppm astaxanthin and sockeye salmon average 40 ppm (Turujman, 1997). Other sources of astaxanthin include processed crustacean wastes from krill, shrimp, crab and crawfish, the fermentative yeast *Phaffia rhodozyma* and chemically synthesized astaxanthin. *Haematococcus pluvialis*, also referred to as *Haematococcus lacustris* or *Sphaerella lacustris*, is a ubiquitous green alga of the order Volvocales, family Haematococcaceae. It is now known that the alga occurs in nature worldwide, where environmental conditions for its growth are favorable and most often found in cooler pools of fresh water such as garden birdbaths.

Under nutrient-rich conditions, Haematococcus is motile and utilizes the available nitrate, phosphate, and other nutrients to grow and reproduce. However, when nutrients become limiting or the pool begins to dry the alga form a protective cell wall and encyst. High concentrations of astaxanthin are produced, and the cells undergo a dormant stage until the next influx of water and nutrients. Cells can remain viable in this encysted stage with its protective astaxanthin for many years. Red cysts are significantly more resistant to strong light and oxygen radicals than green cells, suggesting significant protective roles for astaxanthin (Kobayashi et al., 1992a).

Astaxanthin, is biosynthesized through the isoprenoid pathway, which initiates at acetyl-Co-A and proceeds through phytoene, lycopene, beta-carotene, and canthaxanthin before the last oxidative steps to astaxanthin. Fatty acids are esterified onto the 3' hydroxyl group(s) of astaxanthin after biosynthesis of the carotenoid, and allow it to have more solubility and stability in the cellular environment. The carotenoid fraction of green vegetative cells consists of mostly lutein (75–80%) and beta-carotene (10–20%). Whereas in red cysts, the predominate carotenoid is astaxanthin (Renstrom et al., 1981). Free astaxanthin and its mono- and diesters from Haematococcus have optically pure (3S,3'S)-chirality (Grung et al., 1992 and Renstrom et al., 1981).

Advanced technology has been developed to grow Haematococcus and harnesses the unique properties of the algae to produce very high concentrations of natural astaxanthin. Lots are generally standardized to contain 1.5% (15,000 ppm) astaxanthin, other beneficial carotenoids such as beta-carotene, canthaxanthin, and lutein are also present in lesser amounts. The astaxanthin is predominately in the esterified form, which provides the highest stability. Most importantly, the production process includes a technique which 'cracks' greater than 95% of the cells to enable maximum bioavailability, resulting in a fine dark red powder.

Dried Haematococcus algae, Phaffia yeast powder, or synthetic astaxanthin can be formulated into various food grade oils such as safflower, canola, tocopherols or rice bran and manufactured into gelcaps for convenient ingestion. Alternatively, dried Haematococcus algae, Phaffia yeast powder, or synthetic astaxanthin can be stabilized by various commercial processes and added directly to foods or beverages. Prior Research:

Ultraviolet radiation has long been known to cause epidermis photoaging and skin cancer. SKH 1 hairless mice sensitive to UV light are often used to understand the effects of artioxidants and light-induced polyamines. Polyamines are central to normal growth and activation of polyamine metabolism (putrescine in particular) is implicated in tumor promotion. In one study, female SKH1 hairless mice were weaned at eight weeks and fed six different diets containing 5-ppm beta-carotene, 10-ppm astaxanthin or retinol. After 4 months, one half of each group was exposed to ultraviolet light, sacrificed, and then putrescine, spermidine and spermine concentrations were measured in the epidermis. After irradiation, astaxanthin alone or in combination with retinol was remarkably effective in preventing increases of free putrescine after damage was induced. The putrescine of the control group increased 4.1-fold whereas the groups fed astaxanthin increased only 1.5-fold. Astaxanthin also had a stronger inhibitory effect on putrescine accumulation than dietary retinol. Additionally, spermidine and spermine concentrations were significantly lower in those groups fed astaxanthin. Taken together, the results indicate that astaxanthin exerts a specific action on transglutaminase enzymes to consume these polyamines in response to skin irradiation (Savoure, 1995).

In rat kidney fibroblasts, addition of astaxanthin exhibits superior protection against UVA light-induced oxidative stress compared to lutein and beta-carotene. Cell cultures were grown in differing concentrations of carotenoid-supplemented media and exposed to UVA light for four hours. Subsequently, various parameters were assayed. Catalase (CAT) and superoxide dismutase (SOD) were significantly decreased following the UV insult exposure compared to control cultures, whereas thiobarbituric acid reactive substances (TBARS) were significantly increased. Beta-carotene at a level of 1000 nM and lutein at 100 nM were necessary to protect against UV-induced loss of CAT, whereas it only required 5 nM of astaxanthin. Similarly, levels of 500 nM beta-carotene, 1000 nM of lutein and only 5 nM of astaxanthin were required to protect against loss of SOD activity compared to control cultures. Increases in thiobarbituric acid reactive substances (TBARS) were also measured as indices of oxidative stress. Supplementation of beta-carotene at 100 nM, lutein at 1000 nM and astaxanthin at only 1 nM prevented the UVA-induced increase in TBARS. The authors suggest that carotenoids other than beta-carotene, and particular astaxanthin, may be important biological antioxidants (O'Connor, 1998).

In one contradictory study, SKH hairless mice fed either beta-carotene, lycopene or astaxanthin as sole carotenoid sources tended to have higher probability of epidermal tumors. The authors state that it would be prudent to consume foods with mixed carcotenoids in addition to vitamins E and C, since they are thought to complete the antioxidant cascade (Black, 1998).

Researchers have developed a variety of methods to measure the antioxidant capacity of carotenoids. Some of these assays are conducted in test tubes (in vitro) to better control conditions or within cells themselves (in vivo). Typically, a chemical that generates free radicals or peroxides is mixed with a substrate such as a fatty acid that can become readily oxidized. When the reaction rate is determined, carotenoids or other antioxidants can then be added to determine how it quenches, or slows the peroxidation rate of the fatty acid. Numerous studies exist demonstrating the potent radical scavenging and singlet oxygen quenching properties of astaxanthin (Haila, 1997;Woodall, 1997;Nakagawa, 1997;Oshima, 1993; Tinkler, 1994). It has been demonstrated that astaxanthin is significantly more effective in neutralizing free radicals than beta-carotene and protects against peroxidation of unsaturated fatty acid methyl esters better than canthaxanthin, beta-carotene or zeaxanthin (Terao, 1989; Jorgensen, 1993).

The unique structure of astaxanthin scavenges lipid radicals and effectively breaks peroxide chain reactions (Terao, 1989). Di Mascio utilized a chemiluminescent technique to express the superior singlet oxygen quenching ability of astaxanthin compared to other carotenoids. He also concluded that the effectiveness and potency of astaxanthin was even better expressed at the lower oxygen concentrations found in tissues, as opposed to higher oxygen concentrations normally used with in vitro conditions (Di Mascio, 1989). Many antioxidant studies are conducted under conditions of low vitamin E (tocopherol) or vitamin A to better assess the actual effects of the added carotenoids. In vitamin E-deficient rats, astaxanthin protects the mitochondria from damage caused by lipid peroxidation.

The antioxidant activity of astaxanthin is much greater than vitamin E (Kurashige, 1990). A number of studies have shown that astaxanthin has an activity 80–550 times greater than alpha-tocopherol, also known as vitamin E (Di Mascio, 1989; Ranby and Rabek 1978; Shimidzu, 1996). One prominent researcher has proposed astaxanthin as the 'super vitamin E' (Miki, 1991). Although researchers use different assay systems, the antioxidant activity of astaxanthin has been shown to be approximately 10 times stronger than the antioxidant activity of other carotenoids such as zeaxanthin, lutein, beta-carotene and canthaxanthin (Miki, 1991).

Enzymatic and non-enzymatic antioxidant systems play a vital role in protecting tissues from excessive oxidative damage. Depletion of each of the antioxidant systems increases the vulnerability of various tissues and cellular components to reactive oxygen species (Ji, 1995). There is consistent evidence from human and animal studies that strenuous physical exercise may induce a state wherein the antioxidant defenses of several tissues are overwhelmed by excess reactive oxygen (Sen, 1995). For example, physical exercise causes oxidative stress that leads to the formation of reactive oxygen and nitrogen species (Poulsen, 1998; Caillaud, 1999). This may lead to DNA and muscle tissue damage.

Free radicals generated by oxidative stress have also been shown to change immune function and lead to an inflammatory response (Niess, 1999). Many components of the immune system exhibit adverse change after prolonged, intense exertion. A period of impaired immunity may last from 3 to 72 hours depending on the immune measure (Nieman, 1999). Prolonged stress as a result of excessive exercise can lead to a decline in certain aspects of immune system function such as natural killer cell cytotoxicity or secretory-IgA (Kelly, 1999)

Many researchers recommend the consumption of anti-oxidant compounds to counteract the oxidative damage that occurs free radical accumulation. Human studies have shown that dietary supplementation with antioxidant vitamins such as vitamin E and C have a favorable effect on lipid peroxidation after stress (Derkkers, 1996; Goldfarb, 1993; Kanter, 1998). Beta-carotene and antioxidant coenzyme Q10 have been suggested as dietary supplements to minimize the oxidative damage during stress (Witt, 1992). Selenium dietary supplements have also been shown to reduce free radical formation during exertion in rats (Konda, 1998).

Epidemiological studies have demonstrated a correlation between increased carotenoid intake and the reduced incidence of coronary heart disease and certain cancers, macular degeneration, and increased resistance to viral, bacterial, fungal and parasitic infections (Seddon, 1994; Zhang, 1999, Rao, 1999; Rumi, 1999; Batieha, 1993). Studies indicate that the mechanism for this protective attribute is partly due to the direct enhancement of the immune response by carotenoids. Anticarcinogenic effects of carotenoids are likely attributable to its antioxidant effect, insofar as oxygen radicals are related to the process of cancer initiation and propagation.

Singlet oxygen is also cytotoxic to the immune system by virtue of its ability to catalyze production of free radicals. This action can facilitate degradation of macrophage 25 cell membranes resulting in dysfunction and reduced efficiency of phagocytosis Bendich, 1991). Carotenoids have been shown to enhance both the non-specific and specific immune system and protect cell membranes and cellular DNA from mutation (Bendich A. 1989). Carotenoids have a significant stimulatory effect on the immune system, as seen by the proliferative response of spleen cells and thymocytes during antibody response of mice. Astaxanthin enhances the release of interleukin-1 alpha and tumor necrosis factor alpha in mice to a greater degree than canthaxanthin and beta-carotene. The conclusion of one study was that astaxanthin had the best cytokine-inducing activity and may provide an immunomodulating role (Okai, 1996).

In one series of immune system challenges, astaxanthin enhanced T-helper cell antibody production even when suboptimal amounts of antigen were present. Furthermore, astaxanthin, but not other carotenoids (canthaxanthin, beta-carotene, lutein, lycopene), increased the number of antibody-secreting cells from primed spleen cells (Jyonouchi, 1996). Using human blood, it was shown that astaxanthin enhances the production of IgM, IgA and IgG antibodies in response to T-dependent stimuli (Jyonouchi, 1995a and 1995b). Another study indicates a significant immunomodulating action of astaxanthin for humoral immune responses to T-dependent antigens and the authors suggest that carotenoid supplementation may be beneficial in restoring humoral immune responses in older animals. Furthermore, it was speculated that dietary carotenoids could reduce the chance of developing autoimmunity and malignancies by enhancing T-helper functions and promoting specific antibody responses (Jyonouchi, 1994).

Monocytes are a particular type of white blood cell which contain surface proteins that distinguish cancer cells from normal healthy ones. When these MHC II proteins identify cancer cells they signal the immune system to attack them. Monocytes do not identify cancer cells if the monocytes don't have enough MHC II proteins. It was demonstrated that supplementation with a carotenoid in the diet increases the number of MHC II proteins on monocytes. In turn, subjects had increased production of tumor necrosis factor alpha (TNF-a) which helps kills cancerous and virus-infected cells (Hughs, 1997).

Supplementation with carotenoids increases the number of circulating lymphocytes (T-helper cells), enhances T and B lymphocyte proliferation, improves rejection of foreign tissue, increases killer cell destruction of tumor cells and neutrophil killing of Candida fingi, and inhibits loss of macrophage receptors (Bendich, 1990). Mice fed carotenoids had significantly reduced tumor growth when the primary lesion was excised and then re-challenged with the same tumor (Tomita, 1987). Virus-induced tumors such as murine sarcoma are slowed by carotenoids, as well as adenocarcinoma, squamous cell carcinoma, fibrosarcoma, and chemically induced tumors (Bendich, 1990). These studies present strong evidence that orally administered astaxanthin and other carotenoids can directly affect the immune responses to foreign antigens and cancerous tumors.

In summary, with respect to the prevention ultimately of skin cancers, prevention of sunburn should be the most important goal. Avoiding sun during the period of peak solar radiation from 10 AM to 3 PM and wearing protective clothing including hats offers the best protection against sunburn. Regular use of sunscreens with an adequate sun protection factor (SPF) applied 30 minutes before exposure to sun can also help protect skin. Despite all of the precautions available, people are still exposed to excessive UVR each year and many sunburns result. Thus, in addition to those methods currently known, there remains a need for additional effective sunburn protection and prevention. The easiest form of sunburn prevention would be an oral form of sunburn prevention.

SUMMARY OF THE INVENTION

Astaxanthin is a potent antioxidant, over 500 times more powerful than Vitamin E and 10 times stronger than other carotenoids such as zeaxanthin, lutein, canthaxanthin and beta-carotene. Astaxanthin has also been shown to enhance and modulate the immune system. These effects in combination or separately are able to retard and prevent sunburns, and possibly some resulting skin cancers, when astaxanthin is ingested, injected, or delivered by a cream in a therapeutically effective dose.

Thus one aspect of the invention is to produce an inexpensive means to retard and prevent sunburns and possibly sunburn related cancers.

Another aspect of the invention is to provide a means to retard and prevent sunburns that is ingestible.

A further aspect of the invention is to provide a means to retard and prevent sunburns in a cream formulation for topical application.

Yet another aspect of the invention is to provide a means to retard and prevent sunburns that is injectable.

Another aspect of the invention is to use the unique antioxidant and immune modulation properties of astaxanthin to retard and prevent sunburns, or related cancers.

A still further aspect of the invention is to provide a therapeutically effective dose of astaxanthin in the range of about 1–100 mg per day to retard and prevent sunburns.

These and further aspects of the invention will be shown as illustrated in the following detailed description of the invention, and the appended claims.

DETAILED DESCRIPTION OF THE INVENTION

Astaxanthin is a potent antioxidant with over 10 times the antioxidant activity of other carotenoids such as zeaxanthin, lutein, beta-carotene and canthaxanthin and up to 500 times the antioxidant activity of vitamin E. Further, research has shown that astaxanthin enhances the immune system.

UVR causes sunburns and additionally generates free radicals that have been shown to change immune function and lead to lipid peroxidation and inflammatory response. Human studies have shown that dietary supplementation with antioxidant vitamins such as vitamin E and C have a favorable effect on lipid peroxidation before or after sun exposure. Thus, many researchers recommend the consumption of antioxidant compounds to counteract the oxidative damage that occurs after sun exposure.

With respect to sunburns, it is known that these conditions can result from the stress of UVR exposure. Anti-inflammatory medicines are often recommended to help control the inflammation and reduce the symptoms of sunburns. These medications include the common over the counter medications such as ibuprofen, acetaminophen and aspirin.

Since astaxanthin is a potent antioxidant and can also enhance the immune system, Applicants realized that astaxanthin could be effectively used to counteract UVR light and the oxidative stress and inflammation that results from sunburns.

It has been noted that Haematococcus algae is an excellent source of natural astaxanthin. Advanced technology has been developed to grow Haematococcus and harnesses the unique properties of the algae to produce very high concentrations of natural astaxanthin.

Dried Haematococcus algae, Phaffia yeast powder, or synthetic astaxanthin can be formulated into various food grade oils such as safflower, canola, tocopherols or rice bran and manufactured into gelcaps for convenient ingestion. Alternatively, dried Haematococcus algae, Phaffia yeast powder, or synthetic astaxanthin can be stabilized by various commercial processes and added directly to foods or beverages.

The carotenoid astaxanthin has never been suggested as a dietary supplement to retard or prevent sunburns or related cancers. Nor have the combined properties of astaxanthin as a potent antioxidant and an immune system modulator been previously recognized or proposed as a dietary supplement to retard or prevent sunburns.

Thus, Applicants present a novel treatment and method for retarding and prevention of sunburns, and possibly related cancers resulting from long term sunburn damage.

The invention is a treatment and method of retarding and preventing sunburns by administering a therapeutically effective dose of astaxanthin.

The astaxanthin is preferably administered orally, in doses of between about 1 to about 100 mg per day. Doses of between about 2 to about 10 mg per day are preferable. The dose may be administered to be taken with meals, twice daily.

In addition to an oral administration, a formulation of astaxanthin may also be applied in a cream or injected into the exposed area. Such a dose would also be in the range of about 1 to 100 mg per day.

It is preferable, with an ingestible form of astaxanthin, to begin administering the astaxanthin at least two or three days before sun exposure, and preferably at least a week before exposure, in order to prevent sunburn. However, as seen below in the examples, even ingestion during or after exposure provides beneficial effects. With the topical and injectable treatment, astaxanthin may be administered before, during, or after exposure.

EXAMPLE 1

Haematococcus algae meal containing 1.5% astaxanthin was thoroughly mixed with safflower oil such that the resulting suspension contained 2.0 mg of pure astaxanthin per gram of safflower oil suspension. 500 mg soft gel capsules were produced from the safflower oil suspension such that each soft gel capsule contained 1.0 mg of pure astaxanthin.

One individual was an adult female with extreme propensity for sunburns. The subject had come to Hawaii for vacation and had already sunburned on a 10 minute walk with SPF 50 sunblock cream, long pants and sleeves. She then began taking 2 milligrams of astaxanthin of the above formulation per day. On the eleventh day, she took another walk in the afternoon, on a cloudy day, with long pants, a tee shirt, but without a hat or sunglasses. While 1 mile away from her condo, the clouds dissipated and she was exposed to the full sun while walking back. Normally, she would have experienced a severe case of sunburn but was not affected by the UVR exposure due to the sunscreen properties of the dietary astaxanthin. For the remainder of her vacation, while taking the astaxanthin supplement, she was able to wear shorts outside without sunburn effects.

EXAMPLE 2

An adult male subject is a construction worker in Hawaii and is routinely exposed to the UVR of the sun while working outside. He was often affected by sunblister sores breaking out on his arm after a long day of sun exposure. The individual began taking 4 milligrams of astaxanthin per day derived from Haematococcus algae (as described in the above Example 1). Two milligrams of astaxanthin were consumed with lunch and 2 milligrams with dinner. After 2 weeks of ingesting the astaxanthin the individual was not sensitive to the sun exposure and his blisters began to heal. After a period of 1 month, all of his blisters were healed and sensitivity to the sunlight was noticeably improved.

The individual stopped taking the astaxanthin formulation for two weeks and the blisters and sun sensitivity returned. He then began taking the astaxanthin formulation again at the same dosage and the blisters and sun sensitivity were again ameliorated.

Thus it can be seen, from Example 1, that ingestion before exposure provides sunburn preventive effects, but it is also shown, from Example 2, that oral treatment begun after exposure ameliorates existing sensitivity and prevents future sunburn.

The preventive and ameliorative effects of the topical and injectable treatment are more immediate, as the astaxanthin is applied directly to the affected site.

While the above description and examples disclose preferred embodiments of the invention, there may be variations that, while not specifically described, do not depart from the spirit and scope of the invention as described above and in the appended claims.

What is claimed is:

1. A method to retard and prevent sunburns of the skin, comprising orally administering, to a patient in need thereof, a therapeutically effective dose of a formulation comprising astaxanthin as the single active ingredient.

2. The method according to claim 1 wherein said therapeutically effective dose is in the range of about 1 to 100 mg of astaxanthin per day.

3. The method according to claim 2 wherein said therapeutically effective dose is in the range of about 2 to 10 mg of astaxanthin per day.

4. The method according to claim 1 wherein administration of said therapeutically effective dose is begun before, during or after sun exposure.

5. The method according to claim 4 wherein administration of said therapeutically effective dose is begun two to three days before sun exposure.

6. The method according to claim 4 wherein administration of said therapeutically effective dose is begun a week before sun exposure.

7. The method according to claim 1 wherein said astaxanthin is derived from natural sources.

8. The method according to claim 7 wherein said natural sources are Haematococcus algae, or Phaffia yeast powder.

9. The method according to claim 1 wherein said astaxanthin is produced synthetically.

10. The method according to claim 1 wherein said astaxanthin is in a form esterified with fatty acids.

11. A method to retard and prevent sunburns of the skin, comprising administering, to a patient in need thereof, a therapeutically effective dose of a formulation comprising astaxanthin as the single active ingredient, by injection.

12. The method according to claim 11 wherein said therapeutically effective dose is in the range of about 1 to 100 mg of astaxanthin per day.

13. The method according to claim 12 wherein said therapeutically effective dose is in the range of about 2 to 10 mg of astaxanthin per day.

14. The method according to claim 11 wherein administration of said therapeutically effective dose is begun before, during or after sun exposure.

15. A method to retard and prevent sunburns of the skin, comprising administering, to a patient in need thereof, a therapeutically effective dose of a formulation comprising astaxanthin as the single active ingredient, topically.

16. The method according to claim 15 wherein said therapeutically effective dose is in the range of about 1 to 100 mg of astaxanthin per day.

17. The method according to claim 16 wherein said therapeutically effective dose is in the range of about 2 to 10 mg of astaxanthin per day.

18. The method according to claim 15 wherein administration of said therapeutically effective dose is begun before, during or after sun exposure.

19. A treatment to retard and prevent sunburns of the skin, comprising about 1 to 100 mg of astaxanthin per day, in a formulation comprising astaxanthin as the single active ingredient, administered to a patient in need thereof, orally, topically, or by injection.

20. The treatment according to claim 19 comprising about 2–10 mg of astaxanthin per day administered to said patient, orally, topically, or by injection.

* * * * *